(12) United States Patent
Gardenier et al.

(10) Patent No.: US 6,629,320 B1
(45) Date of Patent: Oct. 7, 2003

(54) FLUID FLOW SYSTEMS AND METHODS

(75) Inventors: W. John Gardenier, Albany, NY (US); Anthony Brennan, Clifton Park, NY (US)

(73) Assignee: Saratoga Spa & Bath Co., Inc., Latham, NY (US)

( * ) Notice: Subject to any disclaimer, the term of this patent is extended or adjusted under 35 U.S.C. 154(b) by 0 days.

(21) Appl. No.: 10/060,055

(22) Filed: Jan. 29, 2002

(51) Int. Cl.[7] ............................................. A61H 33/02
(52) U.S. Cl. ........................ 4/541.5; 4/496; 4/541.1
(58) Field of Search ........................ 4/492, 496, 541.1, 4/541.5, 541.6; 239/18; 362/96, 101

(56) References Cited

U.S. PATENT DOCUMENTS

| | | | | |
|---|---|---|---|---|
| 4,901,379 A | * | 2/1990 | Chalberg et al. | 4/541.5 |
| 5,000,665 A | * | 3/1991 | Moeller | 4/541.6 X |
| 5,122,936 A | * | 6/1992 | Guthrie | 362/101 |
| 5,207,499 A | * | 5/1993 | Vajda et al. | 4/492 X |
| 5,217,292 A | * | 6/1993 | Chalberg | 4/541.1 X |
| 5,245,221 A | * | 9/1993 | Schmidt et al. | 4/541.1 X |

* cited by examiner

Primary Examiner—Robert M. Fetsuga
(74) Attorney, Agent, or Firm—Heslin Rothenberg Farley & Mesiti P.C.; Nicholas Mesiti, Esq.; Victor A. Cardona, Esq.

(57) ABSTRACT

A fluid flow system for a hydrotherapy tub includes a fluid injector and a light source. The fluid injector is adapted to inject fluid to an interior of the hydrotherapy tub and the light source is adapted to direct light toward the interior of the hydrotherapy tub through the fluid injector.

29 Claims, 4 Drawing Sheets

FLUID FLOW SYSTEMS AND METHODS

TECHNICAL FIELD

This invention relates, in general, to hydrotherapy tubs and, in particular, to fluid flow systems and methods for directing light toward interiors of hydrotherapy tubs.

BACKGROUND ART

Hydrotherapy tubs, spa assemblies and like systems have enjoyed increased popularity in recent years. In the majority of such systems, a contained space is at least partially filled with a fluid, such as water, which continuously is circulated throughout the contained space. A fluid directing structure is provided to include one or more jet streams of water and/or air directed into the interior of the contained space to create a certain amount of water turbulence.

In a conventional spa assembly or system, the tub or pool like structure is generally formed of rigid material and permanently mounted or fixed either in ground or above ground at a specific location. Fixed plumbing in the form of rigid material conduits, pumps, heating structures, etc. are then mounted at this given location in communication with the interior of the rigid material tub or pool to create the desired treatment of water being circulated. Hydrotherapy tubs generally have a number of fluid flow outlets or nozzles. Each flow nozzle usually jets water or a water-air froth into the tub. Enhanced hydrotherapy typically results from strategic positioning of these fluid flow nozzles at various locations in the tub. The one or more flow nozzles located throughout the tub generally direct single streams of water from each nozzle to specific locations of the user which aids in hydrotherapy of that location. Some hydrotherapy tubs are equipped with air blowers, which blow air to a plurality of air jets or nozzles located within the tub. These blower nozzles or jets are separate from the jets which eject water or water and air into the hydrotherapy tub.

Spas or tubs also often have decorative lighting to complement the fluid flow outlets or nozzles to enhance relaxation and treatment. Typically, these lights are installed mounted to and/or through a wall of the spa or tub in locations complementary to, but distinct from, those to which fluid flow nozzles are mounted. This results in many holes being created in walls of the spas or tubs. An alternative to directly mounting decorative mounting lighting on walls of a tub or spa is to utilize fiber-optic cables. Specifically, the fiber-optic cables may be illuminated by a remote LED source. Typically, the individual fiber optic cables are routed to individual light emitters distributed about the spa. The use of the fiber-optic cables is advantageous because the sources of light may be separated from the moisture associated with the water contained in the spa. However, the routing of individual cables to distributed emitters not only is tedious to install, but the numerous fiber-optic cables are also susceptible to damage and failure during installation and maintenance.

Thus, a need exists for providing fluid flow and light to interiors of tubs or spas while minimizing the amount of holes through the spas or tubs and minimizing exposure of moisture to the lighting sources.

SUMMARY OF THE INVENTION

The present invention provides, in a first aspect, a fluid flow system for a hydrotherapy tub which includes a fluid injector and a light source. The fluid injector is adapted to inject fluid to an interior of the hydrotherapy tub and the light source is adapted to direct light toward the interior of the hydrotherapy tub through the fluid injector. The fluid injector may be an air jet in fluid communication with a blower for blowing air into the tub.

The present invention provides, in a second aspect, a hydrotherapy tub having an interior portion, a fluid injector, and a light source. The fluid injector is adapted to inject fluid to the interior of the hydrotherapy tub. The light source is adapted to direct light toward the interior portion of the hydrotherapy tub through the fluid injector.

The present invention provides, in a third aspect, a method for directing light to an interior of a hydrotherapy tub which includes directing light toward the interior of the hydrotherapy tub from a light source through a fluid injector.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention will be readily understood from the following detailed description of preferred embodiments taken in conjunction with the accompanying drawings in which:

DETAILED DESCRIPTION OF ONE PREFERRED EMBODIMENT OF THE INVENTION

In accordance with the principles of the present invention, fluid flow systems for hydrotherapy tubs or spas and methods for directing light toward interiors of hydrotherapy tubs or spas are provided.

Figure 1:
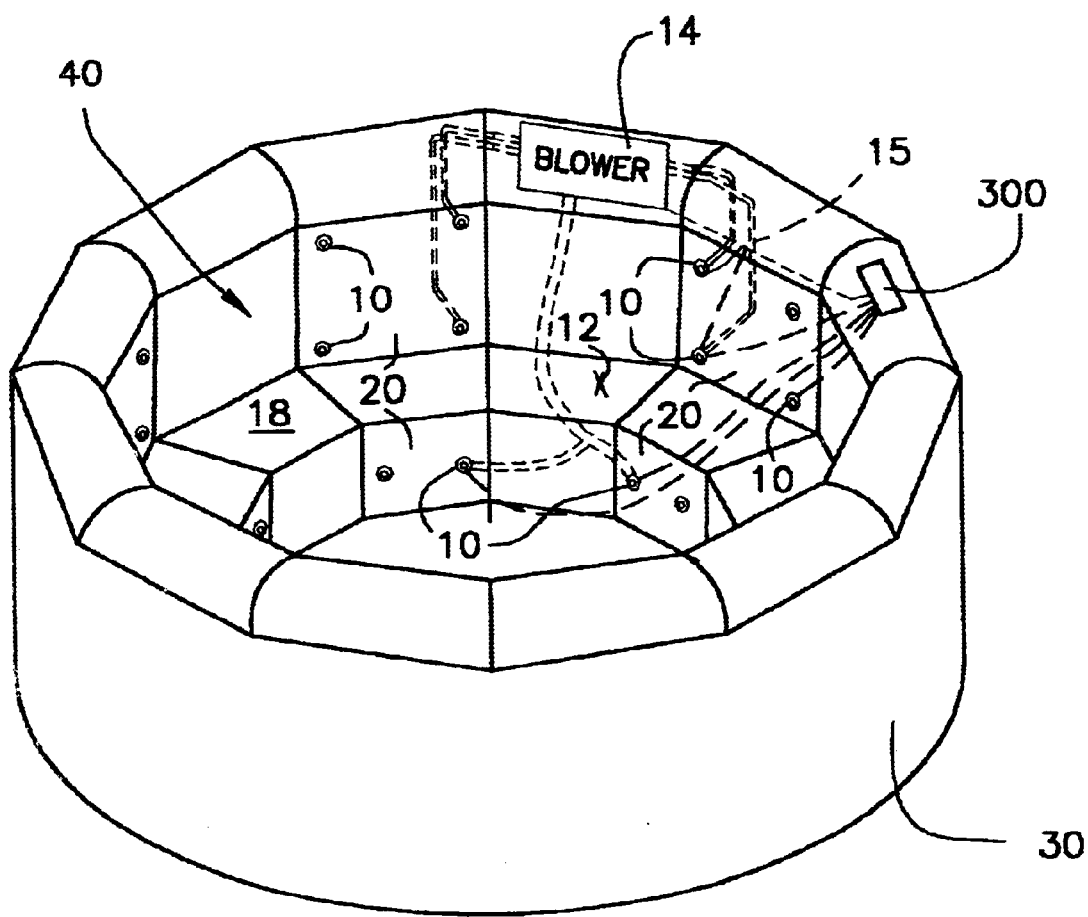
FIG. 1 is a perspective view of a hydrotherapy tub including a plurality of fluid flow systems, in accordance with the present invention.

In an exemplary embodiment depicted in FIG. 1, a fluid flow device 10 in the form of an air jet coupled to an air blower 14 is mounted to an interior surface 18 of a wall 20 or a bottom of a hydrotherapy-tub or spa 30 at one or more locations. For example, spa 30 may include between 8 and 10 fluid flow devices 10 on interior surface 18. Fluid flow device 10 is adapted to inject a fluid, for example, pressurized air from blower 14, to an interior 40 of spa 30. Further, fluid flow device 10 is adapted to have light transmitted therethrough to interior 40 from a light source 220 (FIGS. 3–4) on an opposite side of wall 20 from interior 40.

Figure 2:
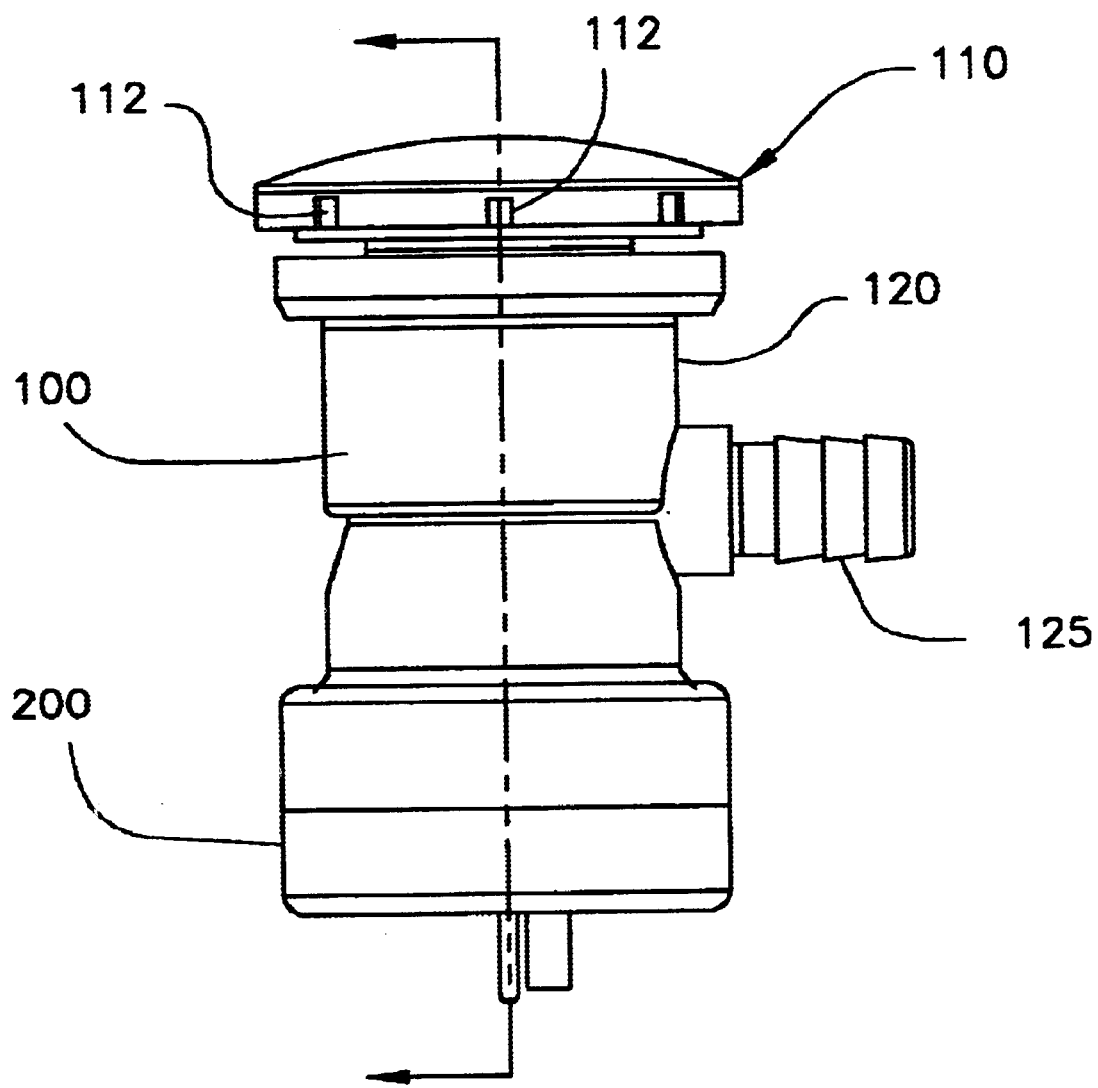
FIG. 2 is a side elevational view of a fluid flow system of FIG. 1.
Figure 3:
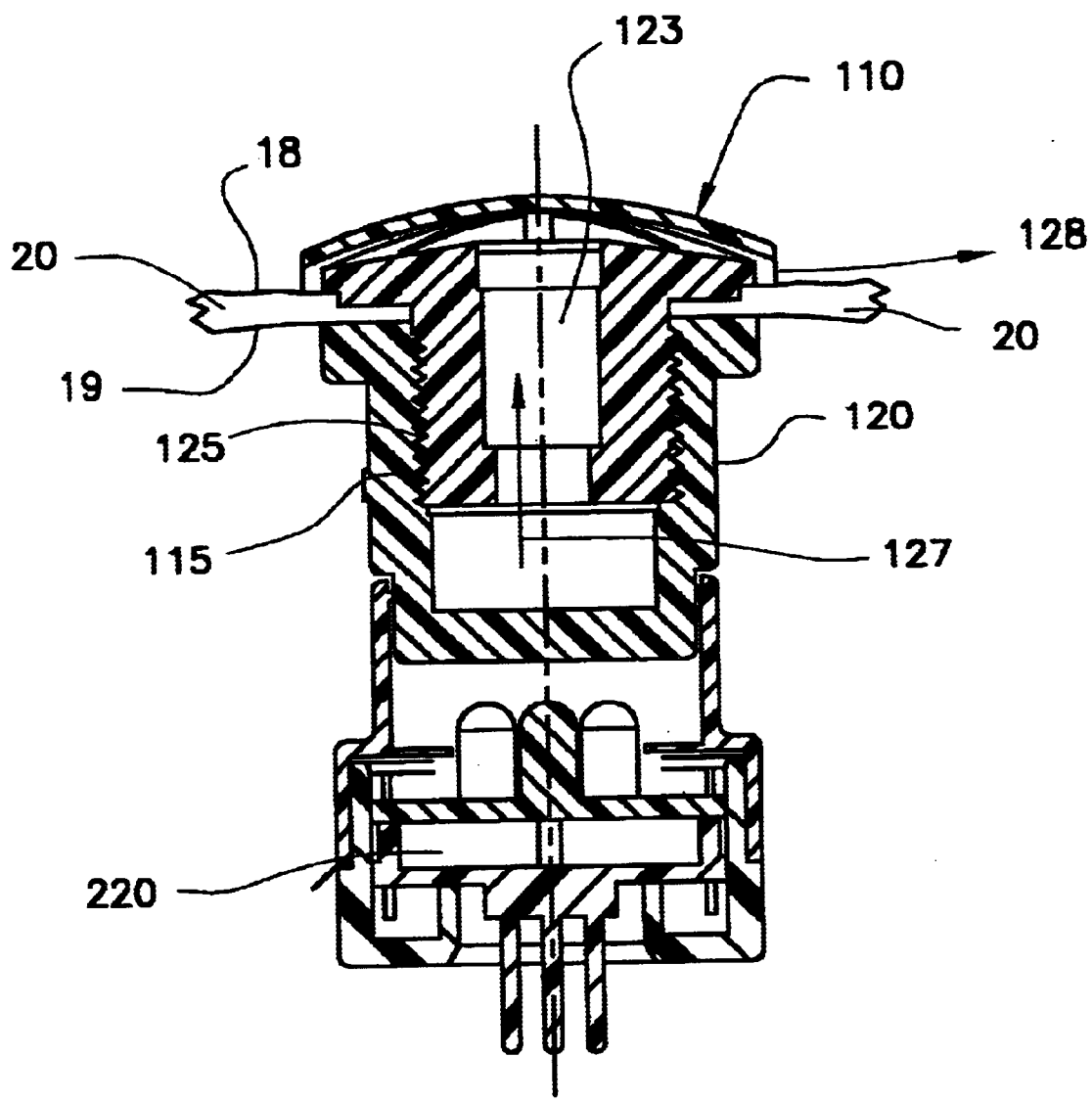
FIG. 3 is a side cross-sectional view of a fluid flow system of FIG. 1 in combination with the wall of the spa of FIG. 1.

Fluid flow device 10 includes a fluid injector 100, e.g., an air jet, and a lighting member 200, as depicted in FIG. 2. Fluid injector 100 further includes an outlet member 110 which engages a body 120. Body 120 further includes an inlet 125 which receives a fluid, for example, pressurized air, which is directed in a direction of an arrow 127 through a center cavity 123 of outlet member 110. Inlet 125 may receive pressurized air though one or more conduits 15 coupled to a source thereof, for example, a water pump (not shown) or an air compressor (not shown). The fluid exits body 120 through one or more outlets 112 of outlet member 110 to interior 40 (FIG. 1) of spa 30 in a direction of a second arrow 128 to provide a hydro-therapeutic effect to a user, as best depicted in FIGS. 2–3. For example, a user may be seated in a position 12 of spa 30 and the fluid may be directed coplanar to wall 20, as depicted in FIG. 1.

Figure 4:
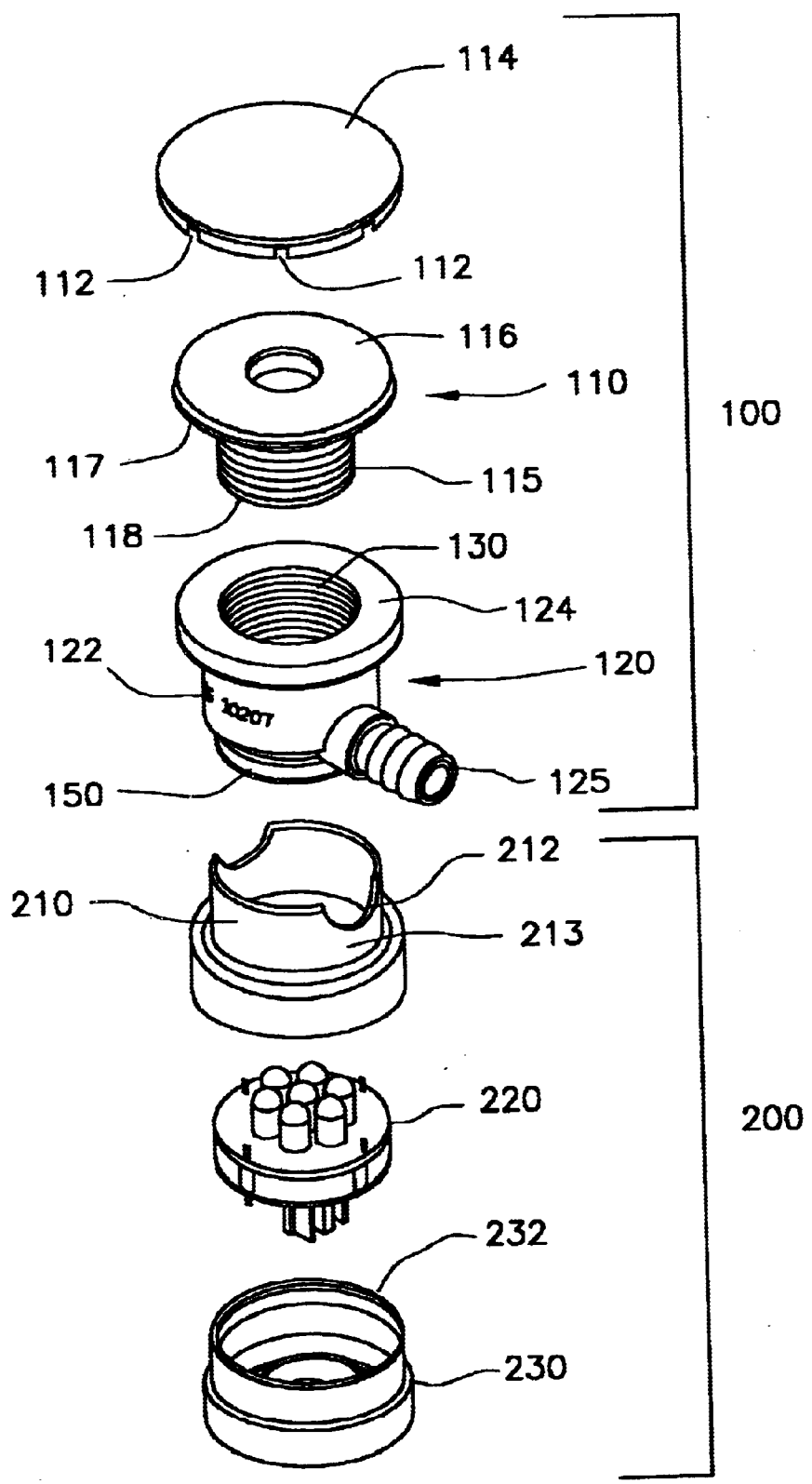
FIG. 4 is an exploded perspective view of a fluid flow system of FIG. 1.

Outlet member 110 includes exterior radial threads 115 for engaging interior radial threads 130 of body 120 which allows outlet member 110 to be screwed into body 120, as depicted in FIGS. 3–4. For example, outlet member 110 may be passed through an opening (not shown) in wall 20 (FIGS. 1 and 3) of spa 30 to engage body 120 to cause fluid injector 100 to be releasably attached to wall 20 (FIGS. 1 and 3). Thus, outlets 112 may be substantially coplanar to wall 20 (FIGS. 1 and 3) and may be under a surface of water in interior 40 (FIG. 1) to provide jets of air to interior 40 (FIG. 1). Body 120 thus may be mounted to an exterior surface 19 of wall 20 (FIG. 3) separated and protected from the water in interior 40 (FIG. 1). Also, outlet member 110 may further include an outlet member cap 114 which is releasably attachable to an outlet member body 116. A number or size of outlets 112 may be varied through a substitution of various outlet member caps 114. Outlets 112 may further be substantially perpendicular to arrow 127.

As best depicted in FIG. 4, fluid injector 100 maybe formed substantially cylindrically. Specifically, body 120 includes a central cylindrical portion 122 and includes a top lip 124 which has a face substantially perpendicular to an axis of body 120 for abutting a lip 117 of outlet member body 116. Further, inlet 125 is located on a longitudinal side of body 120 and a flange 150 is reduced in diameter relative to central portion 122. Outlet member 110 includes protruding portion 118 having exterior radial threads 115, as noted above, for mating with interior radial threads 130 of body 120.

Body 120 of fluid injector 100 is received by lighting member 200, as depicted in FIGS. 2–4. Specifically, flange 150 of body 120 is reduced in diameter as compared to the remainder of fluid injector 100 to allow flange 150 to be received in top light housing 210. Also, top light housing 210 includes a curved portion 212 for receiving a bottom surface of inlet 125. Lighting member 200 further includes a light source 220 and a bottom light housing 230. Light source 220 directs light toward interior 40 (FIG. 1) of spa 30 through fluid injector 100, which may be formed of a transparent or translucent material to allow the light to pass therethrough. For example, fluid injector 100 may be formed of clear polyvinylchloride (PVC), clear ABS plastic or polycarbonate. Also top light housing 210 and bottom light housing 230 may be formed of an opaque and/or reflective material to cause the light produced by light source 220 to be directed toward fluid injector 100. Further, the location of inlet 125 on the side of body 120 allows the light to be directed through body 120 without any shadows or interference from inlet 125.

As best depicted in FIG. 4, lighting member 200 is substantially cylindrical. Top light housing 210 includes a reduced diameter portion 213 for mating with flange 150. Also, bottom light housing 230 includes reduced diameter portion 232 for mating with top light housing 210. Further, it is evident from FIG. 4, that light source 220 is formed of a diameter to allow it to be mounted in bottom light housing 230 at a reduced diameter portion 232.

Light source 220 may be any conventional light source, such as an incandescent or fluorescent light, a light-emitting diode (LED), or fiber optics. One preferred light source is an LED-type light source having embedded hardware and software that provides for a plurality of colors and visual effects. One such light source is an LED-type bulb manufactured by Color Kinetics of Boston, Mass. or Oryan of Vancouver Wash.

Light source 220 may further be controlled by a controller 300 (FIG. 1) coupled to light source 220. Specifically, an intensity of the light produced by light source 220 and/or the time interval at which the light is produced may be controlled by controller 300. The user may program controller 300 to produce these variations in light intensity and/or timing at which the light is produced. Further, multiple light sources 220 may be controlled by controller 300. Also, one or more fluid injectors 100 may be controlled by controller 300 or a separate controller (not shown). Specifically, an intensity of fluid flow and/or a time interval of such flow could be controlled. Moreover, controller 300 may complementarily control one or more fluid injectors 100 with one or more light sources 220.

Thus, fluid flow device 10 includes fluid injector 100 and lighting member 200 which are mounted to wall 20 of tub 30 in a single opening (not shown). The mounting of a light and a fluid injector at a single opening allows a minimal number of openings to be formed in wall 20 because it is not necessary to have separate openings for both a fluid injector and a light. By minimizing the number of openings, time and cost can be saved forming the openings, and the likelihood of water from interior 40 of spa 30 leaking to exterior surface 19 of the wall 20 may be minimized. Moreover, light emitted from light source 220 behind outlets 112 may produce a desirable visual effect as the light passes through the water and/or air at the point of intersection between outlet 1 12 and interior 40.

In one example, fluid injector 100 is mounted to tub wall 20 using epoxy or a similar water-tight sealant. The epoxy forms a fluid-tight seal that safeguards the contents of the hydrotherapy tub. In one preferred embodiment, the epoxy affixes outlet member 110 to body 120 in a position wherein outlet member 110 extends through part of tub wall 20. The body, epoxy, and chamber cooperate to further provide a safe housing for the secure fastening of inlets 125 to one or more fluid supply conduits. Further, one or more sealing washers may be placed between outlet member 110 and body 120 of fluid injector 100 to provide additional water-tight sealing, as will be understood by those skilled in the art.

In one embodiment, the various components, layers, or parts of fluid flow device 10 are molded of ABS plastic. As one example, any number of parts of the fluid flow device 10 may be injection-molded. For instance, any number of the parts of the fluid flow system may be unitary and/or integral. In one example, fluid injector 100 and/or tub wall 20 may be unitary and/or integral, such as may be done by injection molding. As another example, one may selectively secure the system parts by techniques such as heating or gluing. For instance, layers/plates/portions could be heated along certain interfaces.

A hydrotherapy tub may be equipped with multiple cooperating instances of hydrotherapy-tub fluid flow systems (e.g. such as fluid flow device 10), in accordance with the present invention. For instance, several of the fluid flow systems may be positioned in parallel in order to advantageously provide flow in the form of substantially parallel jets of injected fluid. The tub contours already anticipate and promote desirable postures of users in seated and reclined positions. Although the fluid flow systems have been described to comprise air jets, the fluid flow systems may comprise water, or air and water jets.

Outlets 112 may include nozzles of any shape or size and device 10 may include any number of outlets 112. The number of outlets useable for such a system may depend upon the desired velocity of the jets created by such outlets and the size of the pump and/or compressor used to supply fluid, e.g., air, to fluid injector 100. Further, device 10 may include outlets 112 adapted to direct water and/or air in any number of directions. For example, each of outlets 112 may direct water to a single body part of a user.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the following claims.

What is claimed is:

1. A fluid flow system for a hydrotherapy-tub, said system comprising:
   an air injector for injecting air to an interior of the hydrotherapy-tub, said injector having at least one inlet, an outlet member having a cap and at least one outlet, and a cavity for allowing air to flow from said at least one inlet to said at least one outlet; and
   a light source adapted to direct light toward said interior of the hydrotherapy-tub through said cavity and said cap of said outlet member of said air injector.

2. The system of claim 1 wherein said air injector further comprises a body member, and wherein said outlet member and said body member are adapted to engage each other through a wall of the hydrotherapy-tub to mount said fluid injector on said wall.

3. The system of claim 1 wherein at least a portion of said air injector comprises at least one of a translucent material and a transparent material.

4. The system of claim 1 wherein said air injector is adapted to receive the air from a source of air.

5. The system of claim 4 wherein the air comprises pressurized air.

6. The system of claim 1 wherein said plurality of outlets is configured to inject the air toward the interior of the hydrotherapy-tub.

7. The system of claim 6 wherein said plurality of outlets is aligned substantially coplanar to the interior surface of the hydrotherapy-tub.

8. The system of claim 1 wherein said light source comprises at least one of an incandescent light, a fluorescent light, a fiber-optic light, and a light-emitting-diode.

9. The system of claim 1 further comprising a controller coupled to said light source for controlling said light source.

10. The system of claim 9 wherein said controller is programmable to cause said light source to direct light toward the interior of the hydrotherapy tub at least one of at a preselected intensity and at a preselected interval of time.

11. The system of claim 1 further comprising a light housing for holding said light source therein, and wherein said light housing is adapted to receive said fluid injector.

12. The system of claim 11 wherein said light housing is adapted to direct light produced by said light source through said air injector.

13. The system of claim 1 wherein said air injector is adapted to be located below a water surface.

14. The system of claim 1 wherein said air injector comprises
   a first end having at least one outlet for injecting the air toward the interior of the hydrotherapy-tub;
   a second end adjacent to said light source; and
   said inlet being configured to receive the air from an air source, said inlet being located between said first end and said second end.

15. The system of claim 14 wherein said inlet is located on a longitudinal side of said air injector.

16. A method for directing light to an interior of a hydrotherapy tub, said method comprising:
   providing an air injection having an inlet, an outlet member having an outlet, and a cavity allowing air to flow from the inlet to the outlet; and
   directing light toward the interior of the hydrotherapy tub from a light source through the cavity and a cap of the outlet member of the air injector.

17. The method of claim 16 further comprising controlling at least one of an intensity of the light and a time interval of the directing of the light by programming a controller coupled to the light source.

18. The method of claim 16 further comprising injecting air through the air injector to the interior of the hydrotherapy tub.

19. The method of claim 16 wherein the air injector comprises at least one of a transparent material and a translucent material.

20. The method of claim 16 further comprising engaging an outlet member of the air injector with a body of the air injector through a wall of the hydrotherapy tub.

21. The method of claim 20 wherein the engaging causes the outlet member and the body to be releasably mounted on the wall.

22. A hydrotherapy tub, comprising:
   an interior portion;
   an air injector for injecting air to said interior portion of the hydrotherapy-tub, said air injector having at least one inlet, an outlet member having a cap and at least one outlet, and a cavity for allowing air to flow from said at least one inlet to said at least one outlet; and
   a light source adapted to direct light toward said interior portion of the hydrotherapy-tub through said cavity and said cap of said outlet member of said air injector.

23. The hydrotherapy tub of claim 22 wherein at least a portion of said air injector comprises at least one of a translucent material and a transparent material.

24. The hydrotherapy tub of claim 22 wherein said air injector further comprises a body member, and wherein said outlet member and said body member are adapted to engage each other through a wall of the hydrotherapy-tub to mount said air injector on the wall.

25. The hydrotherapy tub of claim 22 further comprising a controller coupled to said light source for controlling said light source, wherein said controller is programmable to cause said light source to direct light toward the interior of the hydrotherapy tub at least one of at a pre-selected intensity and at a preselected interval of time.

26. The hydrotherapy tub of claim 22 wherein said air injector comprises a plurality of outlets for injecting the air toward the interior of the hydrotherapy-tub.

27. The hydrotherapy tub of claim 22 wherein said air injector comprises
   a first end having at least one outlet for injecting the air toward the interior of the hydrotherapy-tub;
   a second end adjacent to said light source; and
   an inlet for receiving the air from an air source, said inlet being located between said first end and said second end.

28. The hydrotherapy tub of claim 27 wherein said inlet is located on a longitudinal side of said air injector.

29. The hydrotherapy tub of claim 27 wherein the air source comprises a source of pressurized air.

* * * * *